United States Patent [19]
Tembe et al.

[11] Patent Number: 6,013,850
[45] Date of Patent: *Jan. 11, 2000

[54] PROCESS FOR THE PREPARATION OF LOW MOLECULAR WEIGHT ALPHA OLEFINS

[75] Inventors: G. L. Tembe; S. Muthukumaru Pillai; Sheo Satish; M. Ravindranathan, all of Gujarat, India

[73] Assignee: Indian Petrochemicals Corporation Limited, Gujarat, India

[ * ] Notice: This patent is subject to a terminal disclaimer.

[21] Appl. No.: 08/826,887

[22] Filed: Apr. 8, 1997

[30] Foreign Application Priority Data

Apr. 9, 1996 [IN] India ............................ 196/96

[51] Int. Cl.$^7$ .................. C07C 2/08; C07C 2/36
[52] U.S. Cl. ............ 585/527; 585/500; 585/502; 585/520; 585/510; 585/511; 585/512; 585/513
[58] Field of Search .................... 585/500, 502, 585/510, 511, 512, 513, 527, 520

[56] References Cited

U.S. PATENT DOCUMENTS

| | | | |
|---|---|---|---|
| 3,981,941 | 9/1976 | Butter | 585/513 |
| 4,689,437 | 8/1987 | Murray . | |
| 4,737,479 | 4/1988 | Frame et al. | 502/117 |
| 5,288,933 | 2/1994 | Kao et al. | 585/513 |

*Primary Examiner*—Elizabeth Wood
*Attorney, Agent, or Firm*—Ladas & Parry

[57] ABSTRACT

A process to maximize the production of low molecular weight alpha olefins from ethylene is disclosed. The process comprises oligomerizing ethylene in the presence of a catalyst, of titanium aryloxide and/or titanium alkoxide; alkyl aluminum halide and triaryl phosphine and/or trialkyl phosphine in the temperature range of 80° C. to 110° C. at substantially low pressures of from 60 to 150 psi. A continuous supply of ethylene is maintained.

15 Claims, No Drawings

PROCESS FOR THE PREPARATION OF LOW MOLECULAR WEIGHT ALPHA OLEFINS

FIELD OF THE INVENTION

The present invention relates to the oligomerization of ethylene in the presence of a catalyst which comprises a titanium aryloxide, and/or titanium alkoxide; alkylaluminum halide and triaryl phosphine and/or trialkyl phosphine in an inert aliphatic or aromatic solvent under conditions in which ethylene is continuously supplied at a constant low pressure to maximize formation of $C_4$–$C_{18}$ alpha olefins.

BACKGROUND OF THE INVENTION

Processes for the catalytic oligomerization of ethylene are well known. It has been shown that these processes produce even numbered carbon olefins having 4 to 50 carbon atoms and terminal double bonds. The preferred olefins are linear alpha olefins with 12 to 18 carbons numbers which are useful in detergents.

The catalysts employed for oligomerization are generally Ziegler-Natta or non-Ziegler type. The non-Ziegler catalysts include organonickel (0) compounds in combination with a modifier such as substituted 2,4-pentanedione as disclosed in U.S. Pat. No. 3,644,564 and employed in the Shell Higher Olefins Process (SHOP).

Ziegler type catalysts employ an alkyl aluminum or its derivative in combination with halides of titanium, zirconium or their complexes. Linear alpha olefins, $C_4$–$C_{20}$+ having average molecular weight 70–300 and 90–100% purity are prepared by ethylene oligomerization in the presence of $TiCl_4$–$RAlCl_2$ (A. Langer, J. Macromolelcular Sci. Chem., A4 (1970) 775).

French Pat. No. 266,992 describes the production of $C_4$–$C_{10}$ alpha olefins in presence of $Zr(OBu)_4$-$THF$-$Et_3Al$. Better control over distribution of alpha olefins is obtained using aryloxide of titanium modified by alkyaluminum sesquihalide as described in Indian Patent Application No. 526/Bom/94 now Indian Patent Application No. 182153 and European Pat. Appln. No. 95300318.3 (1995) (EP 0722 922) $ZrCl_4$-$Et_3 Al_2 Cl_3$-thiols reported in European Patents 241, 596 and 481,435 produced a mixture containing $C_4$ to $C_{30}$ linear alpha olefins and high molecular weight polymers at higher pressures of ethylene.

However, all the prior art processes known to the applicants for oligomerization of ethylene suffer from certain drawbacks such as low degree of selectivity, formation of undesirable polymer low degree of conversion, etc.

Accordingly, it is a primary object of the present invention to provide a process for the oligomerization of ethylene to linear alpha olefins with a higher degree of conversion and selectivity.

It is a further object of the present invention to oligomerize ethylene to linear alpha olefins having 4 to 36 carbon atoms, preferably, with terminal double bonds, in a greater yield.

It is a further object of the present invention to provide a process for converting ethylene to relatively higher proportion of $C_{12}$–$C_{18}$ linear alpha olefins.

Finally it is another object of the present invention to minimize the formation of undesirable high molecular weight polymers.

SUMMARY OF THE INVENTION

The above and further objects of the present invention are achieved by oligomerization of ethylene in the presence of a catalyst system at elevated temperature and low pressure using a continuous supply of ethylene. The process is carried out in the presence of an inert aliphatic or aromatic solvent.

DETAILED DESCRIPTION OF THE INVENTION

According to the present invention, oligomers having ethylene of 4 to 36 carbon atoms, preferably linear olefins are produced at elevated temperature (80° C. to 110° C.) and low pressures (60 psi to 150 psi) under a continuous supply of ethylene in the presence of an inert aliphatic or aromatic solvent and a catalyst system comprising titanium aryloxide and/or titanium alkoxide; alkyl aluminum halide and triaryl phosphine and/or trialkyl phosphine. It has been found according to the invention that higher conversion and selectivity to linear alpha olefins is achieved by maintaining a constant low pressure supply of ethylene. This process is further characterized by ethylene conversion to relatively higher proportion of $C_{12}$–$C_{18}$ linear alpha olefins. In addition another objective of minimizing or eliminating the formation of high molecular weight polymer is achieved by oligomerizing ethylene at higher temperatures.

Accordingly, the present invention provides a process for the production of low molecular weight alpha olefins from ethylene in the presence of an inert aliphatic or aromatic solvent using a multi component catalyst, the first component being titanium aryloxide and/or titanium alkoxide, the second component being alkyl aluminum halide and the third component being triaryl phosphine and/or trialkyl phosphine, the oligomerization being conducted in a reactor vessel at 80° C. to 110° C. at substantially low pressures of about 60 psi to 150 psi under a continuous supply of ethylene.

At least one titanium aryloxide or titanium alkoxide is used. Titanium aryloxides and titanium alkoxides can be used together in the catalyst employed in this invention. The titanium aryloxide and titanium alkoxide may be selected from titanium (IV) cresylates (ortho, meta or para); titanium (IV) 2,6 dimethyl phenoxide, tetra-2-ethyl hexyl titanate, triethanolamine titanate, and diethanolamine titanate.

At least one triaryl phosphine or trialkylphosphine is used. Triarylphosphines and trialkyl phosphines can also be used together in the catalyst.

Preferred catalysts of the invention contain as a first component a titanium (IV) aryloxide derived from any of the ortho, meta or para cresols. Another preferred catalyst contains as a second component dialkyl aluminum halide, preferably diethyl aluminum chloride. The third component is preferably triphenyl phosphine or tributyl phosphine.

The molar ratios of the components of the catalyst of the invention has a bearing on their effectiveness in the production of linear oligomers. It has been found that for the catalyst system described herein the ratio of titanium aryloxide and/or titanium alkoxide to alkyl aluminum halide to trialkyl phosphine and/or triaryl phosphine is preferably be between 1:18:0.5 to 1:75:2. This catalyst system is diluted with an inert solvent like toluene and then used.

A preferred catalyst is of the formula: $Ti(OR_4)$-$Et_xAl_2 Cl_{6-x}$-$PR'_3$ where OR is selected from a group consisting of alkyl and aryl, X is 2, 3 or 4 and R' is aryl or alkyl. It is preferred that oxygen, moisture and other impurities be excluded from the reactants and the solvent.

An important aspect of the invention is the mode of reaction of ethylene with the catalyst present in the inert aliphatic or aromatic solvent. The feed is supplied continuously to the reaction vessel at sufficiently low pressures to prevent the formation of polymer and internal olefins. Continuous feeding of ethylene at the desired low pressure of 60 to 150 psi leads to achieving higher conversions and selectivity of the alpha olefins. It is preferred that the pressure of the the process be maintained between 80 to 90 psi. Useful temperatures for the oligomerization lie between 80° C. to 110° C., while temperatures of 90° C. to 100° C. are preferred.

Useful reaction times range from 5 minutes to 45 minutes while 15 minutes is preferred.

Useful agitator speed ranges from 190 to 500 rpm, while 450–500 rpm is preferred.

When the catalyst system of this invention is used, the oligomerization of ethylene produces a high yield of relatively low molecular weight olefins having 4 to 36 carbon atoms.

The usefulness of the oligomers, made according to the present invention depends on the properties of the oligomerized products. The $C_{12}$–$C_{18}$ alpha olefins are especially suitable as starting material in the manufacture of non-ionic detergents.

The active catalyst solution of the invention is made by mixing the titanium (IV) aryloxide and/or titanium alkoxide (Ti $(OR)_4$) and the triaryl phosphine and/or trialkyl phosphine separately and aging between 15 minutes to 48 hours in the aromatic solvent, the alkyl aluminum halide being added to the vessel along with said mixture of Ti$(OR)_4$ and phosphine. The production of alpha olefins described in the semi-continuous process of the present invention is suitably carried out in a stainless steel vessel with capacity ranging from 5 to 20 liters, preferably in a 5 liter vessel. The volume of liquid comprising solvent and reactants in the vessel can vary from 1.25 liters to 5 liters, preferably 2.5 liters.

The oligomerization product is isolated using a catalyst quenching procedure by adding an aliphatic alcohol, followed a by base and water wash and final recovery by distillation.

The process of the invention is illustrated further by the following examples without limiting the scope of the invention.

EXAMPLE 1

A 5 liter continuously stirred stainless steel vessel were charged with premixed 5.77 gms (0.012 mol) Ti $(OC_6H_4CH_3)_4$ and 6.35 gm (0.024 mol) $PPh_3$ in 1.5 liter dry toluene followed by 54 ml (0.43 mol) $Et_2AlCl$ diluted in 947 ml toluene. The vessel was maintained at 90° C. before catalyst addition. Ethylene was continuously fed at 90 psi for a period of 15 minutes. The temperature rose from 90° C. to 105° C. during the first 5 minutes. The reaction was carried out at 500 rpm. After 15 minutes the vessel was cooled and the contents quenched with 67 ml of n-butanol. The gas and liquid products were then collected and analyzed by gas chromatograph. The product consisted of $C_4$ to $C_{32}$ olefins and the ethylene conversion was about 92% (wt). The selectivity of linear olefins were 1-$C_4$=3.9, 1-$C_6$=4.3, 1-$C_8$=12.4, 1-$C_{10}$=6.7, 1-$C_{12}$=11.6, 1-$C_{14}$=13.0, 1-$C_{16}$=11.3, 1-$C_{18}$=9.6, 1-$C_{20}$=7.5, 1-$C_{22}$=5.9, 1-$C_{24}$=4.4, 1-$C_{26}$=3.2, 1-$C_{28}$=2.5, 1-$C_{30}$=1.6, 1-$C_{32}$=0.4 and polymer=1.7.

EXAMPLE 2

The method of example 1 was followed. A 5 liter vessel was charged with 5.6 gms (0.011 mol) Ti $(OC_6H_4CH_3)_4$ and 6.2 gms (0.022 mol) $PPh_3$ in 1.5 liter toluene followed by 53 ml (0.39 mol) $Et_2AlCl$ in 947 ml toluene. The vessel was maintained at 80° C. while ethylene was fed at 90 psi for a period of 15 minutes. About 106 gms of oligomers consisting mainly of $C_4$ to $C_{32}$ linear alpha olefins and about 6 gm polymer was obtained. The total ethylene conversion at 80° C. was 89% (wt) with the following alpha olefin selectivities: 1-$C_4$=5.5, 1-$C_6$=3.8, 1-$C_8$=8.9, 1-$C_{10}$=4.8, 1-$C_{12}$=7.7, 1-$C_{14}$=8.6, 1-$C_{16}$=8.6, 1-$C_{18}$=8.5, 1-$C_{20}$=7.9, 1-$C_{22}$=7.4, 1-$C_{24}$=6.7, 1-$C_{26}$=5.7, 1-$C_{28}$=4.4, 1-$C_{30}$=3.1, 1-$C_{32}$=2.2 and polymer=5.7.

EXAMPLE 3

The procedure of example 1 was followed: In a 5 liter were added 5.69 gms (0.012 mol) Ti $(OC_6H_4CH_3)_4$ and 6.3 gms (0.024 mol) $PPh_3$ in 1.5 liter toluene. 54 ml (0.4 mol) $Et_2AlCl$ in 946 ml toluene was added to the which was maintained at 100° C. With a stirrer speed of 185 rpm ethylene was fed at 90 psi for a period of 15 minutes continuously. About 92 gms of linear olefins free from polymer was obtained at an ethylene conversion of 91% (wt). Linear olefin selectivity was 1-$C_4$=7.9, 1-$C_6$=9.4, 1-$C_8$=26.2, 1-$C_{10}$=10.7, 1-$C_{12}$=12.2, 1-$C_{14}$=11.2, 1-$C_{16}$=8.9, 1-$C_{18}$=6.3, 1-$C_{20}$=4.0, 1-$C_{22}$=2.3, 1-$C_{24}$=0.9.

EXAMPLE 4

The method of example 1 was followed: In a 5 liter vessel were added 7.6 gms (0.016 mol) Ti $(OC_6 H_4CH_3)_4$ and 8.3 gms (0.032 mol) $PPh_3$ in 1.5 liter toluene. 72 ml (0.57 mol) $Et_2AlCl$ in 928 ml toluene was added to the reactor at a temperature of 100° C. With a stirrer speed maintained at 500 rpm ethylene was fed at 90 psi for a period of 15 minutes. Ethylene conversion was 92% (wt) with selectivities for linear olefins being: 1-$C_4$=6.5, 1-$C_6$=7.4, 1-$C_8$=9.4, 1-$C_{10}$=10.1, 1-$C_{12}$=14.2, 1-$C_{14}$=15.5, 1-$C_{16}$=13.1, 1-$C_{18}$=10.1, 1-$C_{20}$=6.9, 1-$C_{22}$=4.3, 1-$C_{24}$=2.2 and polymer=0.2.

EXAMPLE 5

The method of example 1 was followed. 2.9 gms (0.006 mol) Ti $(OC_6H_4CH_3)_4$ and 3.2 gms (0.012 mol) $PPh_3$ in 1 liter toluene were charged in a 5 liter stainless steel vessel maintained at 90° C. 27.4 ml (0.22 mol) $Et_2 AlCl$ in 222 ml toluene were added and ethylene fed for 15 minutes at 90 psi. The vessel was cooled and quenched with 32 ml n-butanol. Gas chromatographic analysis of products showed 83% (wt) ethylene conversion with alpha olefins selectivity as 1-$C_4$=15.2, 1-$C_6$=5.2, 1-$C_8$=11.0, 1-$C_{10}$=3.8, 1-$C_{12}$=8.4, 1-$C_{14}$=11.1, 1-$C_{16}$=10.2, 1-$C_{18}$=9.3, 1-$C_{20}$=7.5, 1-$C_{22}$=5.3, 1-$C_{24}$=4.4, 1-$C_{26}$=3.5, 1-$C_{28}$=3.1, 1-$C_{30}$=2.0 and polymer=0.04.

EXAMPLE 6

The procedure of example 1 was followed: In a 5 liter vessel were charged 5.6 gms (0.012 mol) Ti $(OC_6 H_4 CH_3)4$ and 6.2 gms (0.024 mol) $PPh_3$ in 1.5 liter toluene followed by 54 ml (0.43 mol) $Et_2 AlCl$ in 946 ml toluene. Ethylene was fed continuously at 90 psi for 30 minutes with vessel temperature at 100° C. and agitator speed at 185 rpm. About 121 gms of oligomers of ethylene were obtained with a total ethylene conversion of 93% (wt). The distribution of alpha olefins was 1-$C_4$=4.5, 1-$C_6$=3.9, 1-$C_8$=10.1, 1-$C_{10}$=4.8, 1-$C_{12}$=10.8, 1-$C_{14}$=13.1, 1-$C_{16}$=12.3, 1-$C_{18}$=11.3, 1-$C_{20}$=9.2, 1-$C_{22}$=7.0, 1-$C_{24}$=5.2, 1-$C_{26}$=3.7, 1-$C_{28}$=2.4, 1-$C_{30}$=1.2 and polymer=0.04.

EXAMPLE 7

The procedure of example 1 was followed: In a 5 liter vessel, were added the catalyst components 5.69 gms (0.012 mol) Ti $(OC_6H_4CH_3)_4$, 3.14 gms (0.012 mol) $PPh_3$ and 54 ml (0.43 mol) $Et_2AlCl$ in 2446 ml toluene. Ethylene was fed to the vessel kept at 100° C. for 15 minutes at 90 psi while stirrer speed as 500 rpm. Product analysis showed a 96% (wt) ethylene conversion with alpha olefin selectivities as $1-C_4=3.4$, $1-C_6=3.1$, $1-C_8=14.3$, $1-C_{10}=7.3$, $1-C_{12}=10.2$, $1-C_{14}=11.5$, $1-C_{16}=11.7$, $1-C_{18}=9.1$, $1-C_2O=7.3$, $1-C_{22}=5.8$, $1-C_{24}=3.9$ $1-C_{26}=2.9$, $1-C_{28}$ 2.2, $1-C_{30}=1.7$, $1-C_{32}=1$, internal olefins=3.5 and polymer=0.75.

EXAMPLE 8

The procedure of example 1 was followed: In a 5 liter reactor were added 4.4 gms (0.0092 mol) Ti $(OC_6H_4CH_3)$ and 4.73 gms (0.018 mol) $PPh_3$ mixed in 1.5 liter toluene followed by 86 ml (0.69 mol) $Et_2AlCl$ in 914 ml toluene at 90° C. vessel temperature. Ethylene was continuously fed at 118 psi pressure for 15 minutes. 356 gms of oligomers of ethylene was obtained. The ethylene conversion was 96.5% (wt) having alpha olefin selectivities of $1-C_4=4.9$, $1-C_6=3.2$ $1-C_8=11.0$ $1-C_{10}=7.9$, $1-C_{12}=11.2$, $1-C_{14}=12.4$, $1-C_{16}=11.7$, $1-C_{18}=10.2$, $1-C_{20}=8.3$, $1-C_2=6.1$, $1-C_{24}=4.4$, $1-C_{26}=3.3$, $1-C_{28}=2.1$, $1-C_{30}=1.4$, $1-C_{32}=1.3$, $1-C_{34}=0.35$.

EXAMPLE 9

The procedure of example 1 was followed. In a 5 liter reactor were added a 20 hrs aged mixture of 4.4 gms (0.0092 mol) Ti $(OC_6H_4CH_3)_4$ and 4.73 gms (0.018 mol) $PPh_3$ mixed in 1.5 liter toluene. 86 ml (0.69 mol) diethyl aluminum chloride in 914 ml toluene was then charged in the reaction vessel kept at 100° C. Ethylene was continuously fed for 15 minutes at 90 psi at an agitator speed of 500 rpm. Analysis of gas and liquid products showed 96% (wt) ethylene conversion with the following alpha olefin selectivities: $1-C_4=7.7$, $1-C_6=9.5$, $1-C_8=19.8$, $1-C_{10}=13.4$, $1-C_{12}=13.7$, $1-C_{14}=11.6$, $1-C_{16}=8.9$, $1-C_{18}=6.9$, $1-C_{20}$ 4.2, $1-C_{22}=1.9$, $1-C_{24}=1.3$, $1-C_{26}=0.76$.

These examples show that the present low pressure process under a continuous supply of ethylene results in a very high conversion of ethylene to linear alpha olefin. Obviously, the product distribution in the process described in the present invention and illustrated in examples 1 to 14 is influenced by process temperature, Ti/Al mole ratio, ethylene pressure, the nature of mixing of catalyst components and agitation. Table I to VII summarize the results of the oligomerization of ethylene under different reaction conditions.

Examples 1 to 9 illustrate the use of triphenylphospluine. The following example 10 illustrates that tributylphosphine can be used in place of triphenylphosphine.

EXAMPLE 10

The procedure of example 8 was followed. In a 5 liter vessel were added 4.38 gms (0.0092 mole) Ti $(OC_6H_4CH_3)_4$ and 4.72 gms (0.018 mole) $PBu_3$ mixed in 1.5 liter toluene followed by 86 ml (0.69 mol) $Et_2AlCl$ in 914 ml toluene at 90° C. vessel temperature. Ethylene was continuously fed at 118 psi for 15 minutes. 107 gms ethylene oligomers were formed. The ethylene conversion was 95.8% (wt) having alpha olefin selectivities of $1-C_4=14$, $1-C_6=12.9$, $1-C_8=16.8$, $1-C_{10}=9.0$, $1-C_{12}=10.7$ $1-C_{14}=9.0$, $1-C_{16}=6.7$, $1-C_{18}=7.0$, $1-C_{20}=4.2$, $1-C_{22}=2.7$, $1-C_{24}=1.7$, $1-C_{26}=1.1$., $1-C_{28}=0.6$, $1-C_{30}=0.3$ and polymer=3.0.

Examples 1 to 10 employ toluene as the solvent. The following examples show that n-octane and p-xylene can also be used as solvents.

EXAMPLE 11

The procedure of example 8 was followed. In a 5 liter vessel were added 4.41 gms (0.0092 mole) Ti $(OC_6H_4CH_3)_4$ and 4.72 gms (0.018 mole) $PPh_3$ mixed in 1.5 liter n-octane followed by 86 ml (0.69 mol) $Et_2AlCl$ in 914 ml n-octane at 90° C. vessel temperature. Ethylene was continuously fed at 118 psi pressure for 15 minutes. 78.1 gms ethylene was consumed. The ethylene conversion was 78.3 %(wt) having alpha olefin selectivities of $1-C_4=21.5$, $1-C_6=12.5$, $1-C_8=35.0$, $1-C_{10}=7.2$, $1-C_{12}=6$, $1-C_{14}=5.1$, $1-C_{16}=3.7$, $1-C_{18}=3.3$, $1-C_{20}=1.7$, $1-C_{22}=1$ and polymer=3.3.

EXAMPLE 12

The procedure of example 8 was followed. In a 5 liter vessel were added 4.38 gms (0.0092 mole) Ti $(OC_6H_4CH_3)_4$ and 4.72 gms (0.018 mole) $PPh_3$ mixed in 1.5 liter p-xylene followed by 86 ml (0.69 mol) $Et_2AlCl$ in 914 ml p-xylene at 90° C. vessel temperature. Ethylene was continuously fed at 118 psi for 15 minutes. 158.5 gms ethylene was consumed. The ethylene conversion was 91.7 %(wt) having alpha olefin selectivities of $1-C_4=7.3$, $1-C_6=9.3$, $1-C_8=12.2$, $1-C_{10}=13.6$, $1-C_{12}=12.6$, $1-C_{14}=11.8$, $1-C_{16}=9.5$, $1-C_{18}=7.0$, $1-C_{20}=6.7$, $1-C_{22}=3.0$, $1-C_{24}=2.0$, $1-C_{26}=1.4$, $1-C_{28}=0.7$, $1-C_{30}=0.5$ and polymer=2.3. The following examples show Ti (IV)-2-ethyl hexanoxide and $EtAlC_2$ can be employed for the oligomerization of ethylene.

EXAMPLE 13

The procedure of example 8 was followed. In a 5 liter vessel were added 5.18 gms (0.0092 mole) Ti $(OCH_2CH[C_2H_5]CH_2[CH_2]2\ CH_3)_4$ and 4.72 gms (0.018 mole) $PPh_3$ mixed in 1.5 liter toluene followed by 86 ml (0.69 mol) $Et_2AlCl$ in 914 ml toluene at 90° C. vessel temperature. Ethylene was continuously fed at 118 psi for 15 minutes. 145 gms ethylene was consumed in this period. The ethylene conversion was 97% (wt) with the following alpha olefin selectivities of: $1-C_4=19.8$, $1-C_6=7.2$, $1-C_8=8.7$, $1-C_{10}=7.7$, $1-C_{12}=11$, $1-C_{14}=8.7$, $1-C_{16}=7.7$, $1-C_{18}=7.3$, $1-C_{20}=5.5$, $1-C_{22}=3.6$, $1-C_{24}=3.3$, $1-C_{26}=2.5$, $1-C_{28}=2$, $1-C_{30}=1.6$, $1-C_{32}=1.1$ and polymer=2.2.

EXAMPLE 14

The procedure of example 8 was followed. In a 5 liter vessel were added 4.4 gms (0.0092 mole) Ti $(OC_6H_4\ CH_3)_4$ and 4.72 gms (0.018 mole) $PPh_3$ mixed in 1.5 liter toluene followed by 72 ml (0.69 mol) $EtAlCl_2$ in 914 ml toluene at 90° C. vessel temperature. Ethylene was fed at 118 psi for 15 minutes. 129 gms ethylene was consumed. The ethylene conversion was 95.9% (wt). Predominantly ethylation of toluene took place. 67.5 gm of ethylene was converted into alpha olefins and polymer with the selectivities: $1-C_4=0.5$, $1-C_6=1.3$, $1-C_{10}=3.2$, $1-C_{12}=4$, $1-C_{14}=5.3$, $1-C_{16}=6.8$, $1-C_{18}=9.5$, $1-C_{20}=8.4$, $1-C_{22}=7.7$, $1-C_{24}=7.9$, $1-C_{26}=10$, $1-C_{28}=10$, $1-C_{30}=9.3$, $1-C_{32}=7.3$, $1-C_{34}=5.3$, $1-C_{36}=2.7$ and polymer=0.7.

TABLE I

Effect of molar ratio of $Et_2AlCl$ to $Ti(OC_6H_4CH_3)_4$

| Run | Mole ratio Al/Ti | Speed rpm | $C_2H_4$ conv. wt % | $1-C_4$ | Selectivity $1-C_6$ to $1-C_{10}$ | $1-C_{12}$ to $1-C_{18}$ | $1-C_{20}+$ | Poly |
|---|---|---|---|---|---|---|---|---|
| 1 | 18 | 500 | 82.4 | 4.7 | 12.1 | 50.5 | 32.1 | 0.6 |
| 2 | 25 | 500 | 85.3 | 2.7 | 13.4 | 43.5 | 40.1 | Nil |
| 3 | 36 | 500 | 91.5 | 4 | 23.4 | 45.5 | 25.5 | 1.7 |
| 4 | 50 | 500 | 91.8 | 5 | 33.5 | 44.1 | 17.2 | Nil |
| 5 | 75 | 500 | 94.5 | 5.8 | 47.4 | 39.3 | 7.1 | — |
| 6 | 18 | 185 | 77 | 7.9 | 22.5 | 43.3 | 25.9 | 0.3 |
| 7 | 36 | 185 | 91.3 | 7.9 | 46.3 | 38.6 | 7.2 | Nil |
| 8 | 75 | 185 | 96.3 | 16.5 | 64.7 | 17.8 | 1 | Nil |

$C_2H_4$ = 90 psi (continuous feed)
Temperature = 100° C.
Process Time = 15 minutes
Liquid volume = 1.5 liters
Catalyst = $Ti(OC_6H_4CH_3)_4$—$Et_2AlCl$—$PPh_3$ $Ti(OC_6H_4CH_3)_4$/liter of Solvent = 2.27 g
$Ti(OC_6H_4CH_3)_4$: $PPh_3$ = 1:2

TABLE II

Effect of reaction time on ethylene oligomerization

| Run | Al/Ti mole ratio | $C_2H_4$ conv. wt % | Time min | $1-C_4$ | Selectivity $1-C_6$ to $1-C_{10}$ | $1-C_{12}$ to $1-C_{18}$ | $1-C_{20}+$ | Poly |
|---|---|---|---|---|---|---|---|---|
| 1 | | 93.8 | 15 | 10.2 | 55.4 | 31.4 | 2.8 | 0.1 |
| 2 | | 96.8 | 21 | 5.5 | 26.5 | 47.2 | 20.7 | 0.004 |
| 3 | | 96.6 | 30 | 4.4 | 21.6 | 46 | 27.9 | Nil |
| 4 | | 97.5 | 45 | 3.2 | 4.8 | 34.2 | 57.5 | 0.14 |

Ethylene pressure = 90 psi (continuous feed)
Temperature = 100° C.
= 75
Speed (rpm) = 500
Liquid volume = 2.5 liters
Catalyst system = $Ti(OC_6H_4CH_3)_4$—$Et_2AlCl$—$PPh_3$
$Ti(OC_6H_4CH_3)_4$/liter = 1.72 g
$Ti(OC_6H_4CH_3)_4$: $PPh_3$ = 1:2

TABLE III

Effect of temperature on ethylene oligomerization

| Run | Al/Ti | $C_2H_4$ conv. wt % | Temp. °C. | $1-C_4$ | Selectivity $1-C_6$ to $1-C_{10}$ | $1-C_{12}$ to $1-C_{18}$ | $1-C_{20}+$ | Poly |
|---|---|---|---|---|---|---|---|---|
| 1 | 36 | 89 | 80 | 5.5 | 17.4 | 33.4 | 37.4 | 6.2 |
| 2 | 36 | 91 | 100 | 4.0 | 23.4 | 45.5 | 25.5 | 1.7 |

Catalyst = $Ti(OC_6H_4CH_3)_4$—$Et_2AlCl$—$PPh_3$
$C_2H_4$ = 90 psi (continuous feed)
Process Time = 15 minutes
Liquid volume = 2.5 liters
$Ti(OC_6H_4CH_3)_4$/liter of solvent = 2.27 g
$Ti(OC_6H_4CH_3)_4$: $PPh_3$ = 1:2

TABLE IV

Effect of Ethylene pressure

| Run | Al/Ti mole ratio | Press psi | $C_2H_4$ conv. wt % | $1-C_4$ | Selectivity $1-C_6$ to $1-C_{10}$ | $1-C_{12}$ to $1-C_{18}$ | $1-C_{20}+$ | Poly |
|---|---|---|---|---|---|---|---|---|
| 1 | 75 | 118 | 96.5 | 4.9 | 22.2 | 45.5 | 27.3 | Nil |
| 2 | 75 | 90 | 93.8 | 10.2 | 55.4 | 31.4 | 2.8 | 0.1 |
| 3 | 75 | 59 | 96 | 13.5 | 58.3 | 26 | 2 | 0.1 |
| 4 | 36 | 90 | 91.2 | 6.5 | 26.9 | 52.9 | 13.4 | 0.2 |
| 5 | 36 | 118 | 93.3 | 3.9 | 8.5 | 41.9 | 44 | 1.5 |

Temperature = 100°
Time = 15 minutes
Speed (rpm) = 500
Catalyst system = $Ti(OC_6H_4CH_3)_4$—$Et_2AlCl$—$PPh_3$
Liquid volume = 2.5 liters
$Ti(OC_6H_4CH_3)_4$/liter of solvent = 1.72 g
$Ti(OC_6H_4CH_3)_4$: $PPh_3$ = 1:2
a$Ti(OC_6H_4CH_3)_4$/liter = 3 g

TABLE V

Influence of C2 on oligomerization of ethylene

| Run | $Ti(OC_6H_4CH_3)_4$ g/liter of solvent | $C_2H_4$ conv. wt % | $1-C_4$ | Selectivity $1-C_6$ to $1-C_{10}$ | $1-C_{12}$ to $1-C_{18}$ | $1-C_{20}+$ | Poly |
|---|---|---|---|---|---|---|---|
| 1 | 3 | 91.2 | 6.5 | 26.9 | 52.9 | 13.4 | 0.2 |
| 2 | 2.27 | 91.5 | 4 | 23.4 | 45.5 | 25.5 | 1.7 |
| 3 | 1.72 | 90.8 | 3 | 20.1 | 41.9 | 33.5 | 1.3 |

Ethylene pressure = 90 psi (continuous feed)
Temperature = 100°
Al/Ti (mole ratio) = 36
Time = 15 minutes
Liquid volume = 2.5 liter

TABLE VI

Influence of agitation on oligomerization of ethylene

| Run | Speed | $C_2H_4$ conv. wt % | $1-C_4$ | Selectivity $1-C_6$ to $1-C_{10}$ | $1-C_{12}$ to $1-C_{18}$ | $1-C_{20}+$ | Poly |
|---|---|---|---|---|---|---|---|
| 1 | 500 | 91.5 | 4 | 23.4 | 45.5 | 25.5 | 1.7 |
| 2 | 350 | 89.8 | 6.9 | 26 | 44.2 | 22 | 0.3 |
| 3 | 185 | 91.3 | 7.0 | 46.3 | 38.6 | 7.2 | Nil |

$C_2H_4$ = 90 psi (continuous feed)
Temperature = 100° C.
Liquid volume = 2.5 liters
Time = 15 minutes
Catalyst = $Ti(OC_6H_4CH_3)_4$—$Et_2AlCl$—$PPh_3$
Al/Ti (mole ratio) = 36

TABLE VII

Effect of $Ti(OC_6H_4CH_3)_4$:$PPh_3$ Molar Ratio on Ethylene Oligomerization

| Run | Ti:$PPh_3$ ratio | $C_2H_4$ conv. wt % | $1-C_4$ | Selectivity $1-C_6$ to $1-C_{10}$ | $1-C_{12}$ to $1-C_{18}$ | $1-C_{20}+$ | Poly |
|---|---|---|---|---|---|---|---|
| 1 | 1:2 | 91.5 | 4 | 23.4 | 45.5 | 25.5 | 1.7 |
| 2 | 1:1 | 89 | 6.9 | 26 | 44.2 | 22 | 0.3 |

TABLE VII-continued

Effect of Ti(OC$_6$H$_4$CH$_3$)$_4$:PPh$_3$ Molar Ratio on Ethylene Oligomerization

| Run | Ti:PPh$_3$ ratio | C$_2$H$_4$ conv. wt % | 1-C$_4$ | Selectivity 1-C$_6$ to 1-C$_{10}$ | 1-C$_{12}$ to 1-C$_{18}$ | 1-C$_{20}$ + | Poly |
|---|---|---|---|---|---|---|---|
| 3 | 1:0 | 91.3 | 7.9 | 46.3 | 38.6 | 7.2 | Nil |

C$_2$H$_4$ = 90 psi (continuous feed)
Temperature = 100° C.
Catalyst = Ti(OC$_6$H$_4$CH$_3$)$_4$—Et$_2$AlCl—PPh$_3$
Al/Ti (mole ratio) = 36
Speed (rpm) = 500
Liquid volume = 2.5 liters

TABLE VIII

Effect of Aging Time of Ti(OC$_2$H$_4$CH$_3$)$_4$—PPh$_3$ on Oligomerization of ethylene

| Run | C$_2$H$_4$ conv. wt % | Aging time (hrs) | 1-C$_4$ | Selectivity 1-C$_6$ to 1-C$_{10}$ | 1-C$_{12}$ to 1-C$_{18}$ | 1-C$_{20}$ + | Poly |
|---|---|---|---|---|---|---|---|
| 1 | 93.8 | 0.16 | 10.2 | 55.4 | 31.4 | 2.8 | 0.1 |
| 2 | 95.7 | 20 | 7.7 | 42.7 | 41.2 | 8.3 | — |
| 3 | 95 | 48 | 8 | 36.8 | 42.9 | 12.1 | 0.1 |

Ethylene pressure = 90 psi (continuous feed)
Temperature = 100°
Al/Ti (mole ratio) = 75
Speed (rpm) = 500
Liquid volume = 2.5 liters
Catalyst system = Ti(OC$_6$H$_4$CH$_3$)$_4$—Et$_2$AlCl—PPh$_3$
Ti(OC$_6$H$_4$CH$_3$)$_4$/liter of solvent = 1.72 g
Ti(OC$_6$H$_4$CH$_3$)$_4$: PPh$_3$ = 1:2

We claim:

1. A process for the production of low molecular weight linear alpha olefins of 4 to 36 carbon atoms from ethylene which comprises subjecting ethylene to oligomerization in an inert aliphatic or aromatic solvent, said oligomerization being carried out in the presence of a catalyst, said catalyst comprising a titanium component, an alkyl aluminum halide component and a phosphine component, said titanium component selected from the group consisting of titanium aryloxide and titanium alkoxide, and said phosphine component selected from the group consisting of triaryl phosphine and triaryl phosphine at a temperature in the range of 80° C. to 110° C. at pressures of from 60 to 150 psi under a continuous supply of ethylene.

2. The process as claimed in claim 1, wherein the process is performed in a semi-continuous mode with said ethylene being fed continuously at a constant pressure throughout the entire period of the process.

3. The process as claimed in claim 1, wherein the catalyst is represented by the formula:

$$Ti(OR)_4\text{-}Et_xAl_2Cl_{6-x}\text{-}PR'_3$$

where R represents alkyl or aryl; x is 2, 3 or 4 and R' represents aryl or alkyl.

4. The process as claimed in claim 1, wherein the alkyl aluminum halide is reacted with the titanium aryloxide, or titanium alkoxide or a mixture thereof in a mole ratio from 18:1 to 75:1.

5. The process as claimed in claim 1, wherein the ethylene pressure is between 60 to 150 psi.

6. The process as claimed in claim 1, wherein the temperature is from 90° C.–100° C.

7. The process as claimed in claim 1, wherein the concentration of said titanium component is from 1.7 to 3 grams per liter of solvent.

8. The process as claimed in claim 1, wherein the process is carried out for a time of about 5 to 45 minutes.

9. The process as claimed in claim 1, wherein the titanium is premixed with the phosphine and aged for a period from 15 min to 48 hours prior to charging in the vessel where the process is carried out.

10. The process as claimed in claim 1, wherein the solvent is toluene, xylene octane.

11. The process as claimed in claim 1, wherein the ratio of titanium aryloxide titanium alkoxide or a mixture thereof to alkyl aluminum halide to triaryl phosphine trialkyl phosphine or a mixture thereof is 1:18:0.5 to 1:75:2.

12. The process as claimed in claim 1, wherein the titanium component is selected from the group consisting of titanium tetra ortho cresylate, titanium tetra meta cresylate, titanium tetra para cresylate, titanium tetra 2,6 dimethyl phenoxide, titanium tetra-2-ethylhexanate, triethanolamine titanate and diethanolamine titanate.

13. The process as claimed in claim 13, wherein the alkyl aluminum halide component is diethyl aluminum chloride.

14. The process as claimed in claim 1, wherein the phosphine component is a triaryl phosphine and is triphenyl phosphine.

15. The process as claimed in claim 1, wherein the phosphine component is a trialkyl phosphine and is tributylphosphine.

* * * * *